(12) United States Patent
Feinsod

(10) Patent No.: US 7,011,666 B2
(45) Date of Patent: Mar. 14, 2006

(54) INCISING APPARATUS FOR USE IN CATARACT SURGERY

(76) Inventor: Matthew Feinsod, 4F Nassau Dr., Great Neck, NY (US) 11021

( * ) Notice: Subject to any disclaimer, the term of this patent is extended or adjusted under 35 U.S.C. 154(b) by 393 days.

(21) Appl. No.: 10/100,884

(22) Filed: Mar. 19, 2002

(65) Prior Publication Data
US 2002/0091402 A1 Jul. 11, 2002

Related U.S. Application Data

(63) Continuation of application No. 09/507,703, filed on Feb. 18, 2000, now Pat. No. 6,379,370.

(51) Int. Cl.
A61F 9/00 (2006.01)

(52) U.S. Cl. .................. 606/107; 606/166; 606/167; 30/301

(58) Field of Classification Search ............. 606/107, 606/167, 170, 179, 166, 161, 162, 113; 30/301; D7/672
See application file for complete search history.

(56) References Cited

U.S. PATENT DOCUMENTS

| 915,611 | A | | 3/1909 | Lane |
| 4,732,154 | A | | 3/1988 | Shiber |
| 4,766,897 | A | | 8/1988 | Smirmaul |
| 5,123,906 | A | * | 6/1992 | Kelman ................ 606/107 |
| 5,135,530 | A | | 8/1992 | Lehmer |
| 5,269,787 | A | | 12/1993 | Cozean, Jr. et al. |
| 5,728,117 | A | | 3/1998 | Lash |
| 5,860,987 | A | * | 1/1999 | Ratcliff et al. ............. 606/113 |
| 6,142,996 | A | | 11/2000 | Mirhashemi et al. |

* cited by examiner

Primary Examiner—Julian W. Woo
(74) Attorney, Agent, or Firm—Frommer, Lawrence & Haug LLP; Matthew K. Ryan, Esq.

(57) ABSTRACT

An incising apparatus for cataract surgery is provided. The incising apparatus includes a handle having a proximal end and a distal end. A circular cutting band is adapted to slide along the handle. At least one stopper element is provided in the vicinity of the proximal end of the handle. The at least one stopper element is positioned within the interior of the circular band so as to restrict the motion of the circular band relative to the handle.

6 Claims, 4 Drawing Sheets

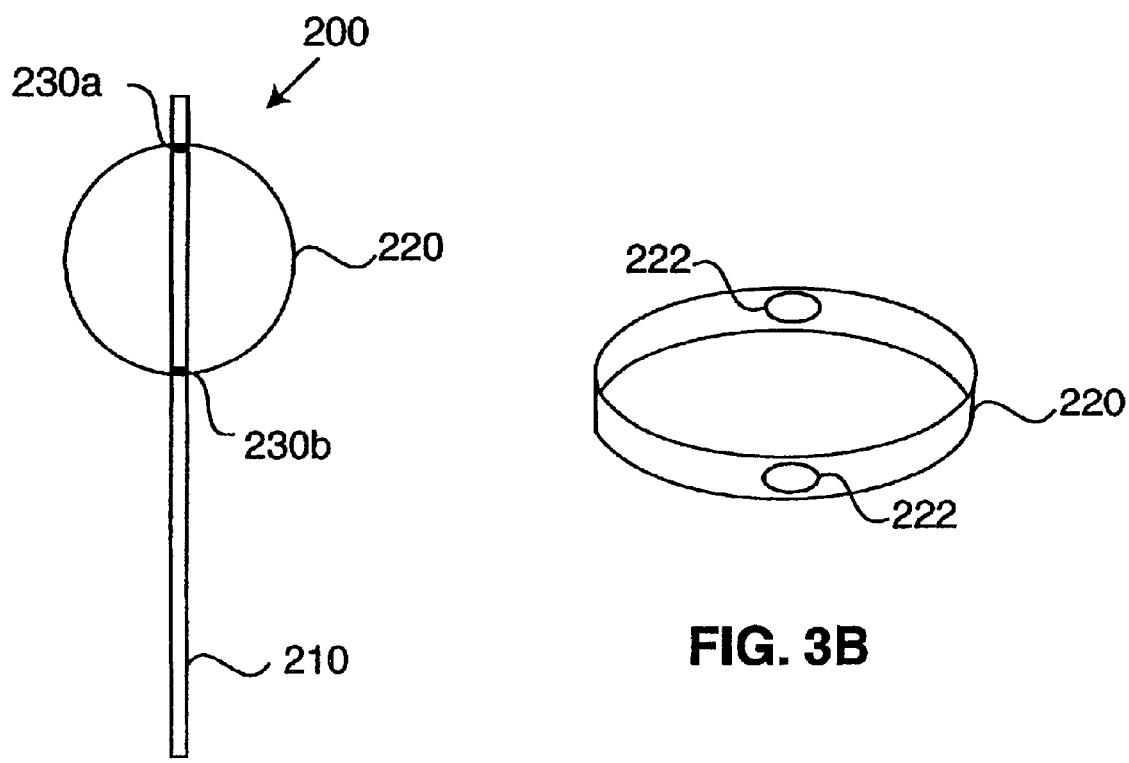
FIG. 3A
FIG. 3B
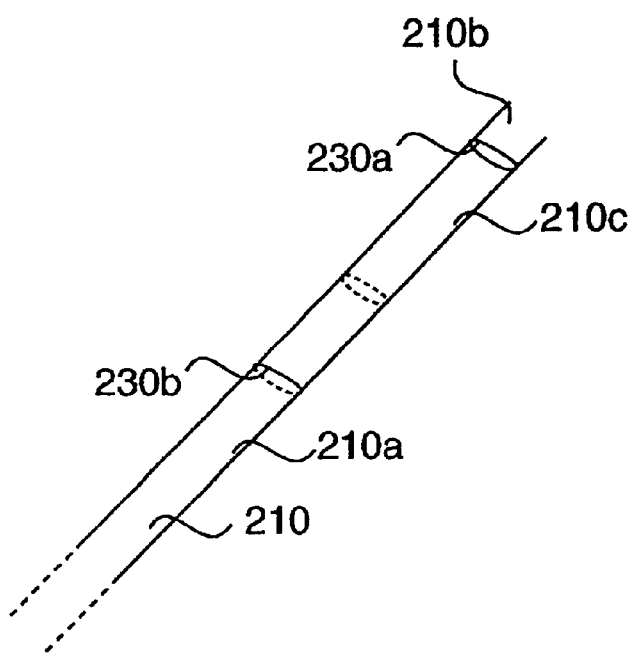
FIG. 3C

INCISING APPARATUS FOR USE IN CATARACT SURGERY

CROSS REFERENCE TO RELATED APPLICATIONS

This application is a continuation of application Ser. No. 09/507,703, filed Feb. 18, 2000, now U.S. Pat. No. 6,379,370.

BACKGROUND OF THE INVENTION

1. Field of the Invention

The invention relates generally to an apparatus used in the field of ophthalmology and more particularly to an incising apparatus used in cataract surgery.

2. Description of the Related Art

The lens of a human eye is a transparent, biconvex crystalline structure located just behind the iris of the eye. The lens substance is contained within an elastic, transparent lens capsule, similar in structure to the substance of a grape being held inside its skin. This lens capsule has a relatively thin cross section, with an average thickness of between 14 microns to 21 microns at its anterior surface.

Cataracts occur when the lens substance opacifies, obscuring the passage of light therethrough and resulting in a decrease in the clarity of a patient's vision. Cataract surgery involves removing the opacified lens and typically replacing it with an artificial intraocular lens implant. The preferred method of routine cataract surgery is referred to as extracapsular cataract extraction. In this procedure the lens is removed through an opening formed in the anterior lens capsule. The remaining portion of the lens capsule is left in place to hold the lens implant that is to be introduced. More modern extracapsular cataract extractions involve the phacoemulsification technique, enabling a smaller surgical incision. The phacoemulsification instrument uses ultrasonic power to fragment the lens nucleus and aspirate the lens contents from the eye. This technique theoretically results in fewer complications, faster healing, and more rapid visual rehabilitation.

A critical and most delicate step in the cataract extraction procedure is the anterior capsulorrhexis step, where a circular opening is created in the thin anterior surface of the lens capsule to obtain access to the lens substance. Prior to starting the capsulorrhexis step, a viscoelastic substance is injected into the eye through a small corneal incision of approximately 1.5 mm (the side port or "paracentesis" port) to maintain proper anterior chamber depth. In current methods, a larger corneal or corneal-scleral incision of 2.0–3.0 mm is then created approximately 3 clock hours from the paracentesis port to accommodate the maneuvering involved in the subsequent capsulorrhexis procedure. A bent sharp-tipped instrument is inserted into the anterior chamber of the eye to make a linear incision in the capsule and to create a small flap. This instrument is then removed, and a forceps is inserted to grasp the newly created free flap. The free flap is delicately manipulated in a circular motion to peel a continuous circular tear in the anterior capsule.

Often, during insertion and manipulation of the forceps, some viscoelastic material inadvertently leaks from the larger corneal incision. This material is critical to maintain the anterior chamber depth and to allow for the successful completion of the circular capsulorrhexis step. Thus, when this material leaks, the forceps must be removed from the eye and more viscoelastic material must be injected. This prolongs the tedious process and increases the risk of error such as a radial tear in the anterior capsule. Because the anterior lens capsule is similar to a cellophane wrapping material, the tear is frequently inadvertently initiated in an undesirable direction, leading to such a dangerous radial tear. A radial tear is dangerous because it results in decreased structural integrity of the lens capsule, and may lead to serious complications, such as the lens falling to the back of the eye or the spillage of vitreous into the anterior chamber intraoperatively. Therefore, it is critical that the tear be continuous and circular, to provide a more stable smooth edge to the opening and to avoid these subsequent radial tears.

The majority of cataract surgeons prefer a round, 5–6.0 mm anterior capsular opening. This size and shape opening allows for better fixation of the nucleus during phacoemulsification and better centration and stability of the intraocular lens implant. Due to the technical difficulty in achieving a capsular opening of optimal size and shape, the anterior capsulorrhexis step may be unreliable, unpredictable, and inconsistent.

U.S. Pat. No. 4,766,897 issued to Smirmaul describes an anterior lens capsule incising apparatus 10. Its forward portion, including a loop 18, can be inserted through a passage wound cut on the corneoscleral tissue of an eye, and disposed above the anterior lens capsule of the eye. A rotatable circular cutting blade 20 of the incising apparatus cuts a circular incision on the anterior lens capsule. The disadvantage of this incising apparatus described in Smirmaul is that it requires a wide passage wound cut on the corneoscleral tissue. The diameter of the rotatable circular cutting blade 20 of Smirmaul is about 6.0 mm, which is the necessary size for cutting an adequate incision on the anterior lens capsule for surgery. Therefore the overall diameter of the circular blade holder must be at least 7.0 mm. This requires that the width of the passage wound cut on the corneoscleral tissue be not less than 7.0 mm, which is wide by eye surgery standards. It is desirable to have the width of the passage wound cut on the corneoscleral tissue as narrow as possible, because a wider wound requires more surgical closing procedures and increases the period of convalescence.

U.S. Pat. No. 5,135,530 issued to Lehmer describes a circular cutting blade having a deformable circular shape with a diameter of not less than 5.0 mm. Additionally, the described preferred anterior lens capsule incising apparatus is able to pass through a narrow corneoscleral tissue wound having a width of not more than 4.0 mm. This deformable circular cutting ring is provided between the forward positions of two elongated arms. The two elongated arms cross each other and are hinged together at the crossing joint. The rearward portion of the two arms are spring biased to keep the forward portion of the two arms spaced apart during use, such that the deformable circular cutting ring maintains its original circular shape. When the rearward portions of the two arms are squeezed toward each other, the forward portions of the two arms similarly move toward each other to compress the deformable circular cutting ring into a narrow elliptical shape. The overall width of the narrow elliptical shaped deformable circular cutting ring and the forward portions of the two elongated arms is less than 4.0 mm. Thus, the narrow elliptical shaped deformed cutting ring and forward portions of the two elongated arms can be inserted into the anterior chamber of the eye through a narrow corneoscleral tissue wound of about 4.0 mm in width. The crossing joint of the two elongated arms is located at or in the vicinity of the corneoscleral tissue wound. Once inside the anterior chamber of the eye, the rearward portions of the two arms are released, so that the forward portions of the two arms move away from each other to allow the deformable circular cutting ring to return to its original circular shape. Then the full size circular cutting ring is pressed onto the anterior lens capsule to cut an adequate sized circular incision so the natural crystalline lens of the eye can be removed and an artificial intraocular lens can be implanted therein. The deformable circular cutting ring is taken out of the anterior chamber through the narrow wound on the corneoscleral tissue by again compressing it into a narrow elliptical shape as noted above.

U.S. Pat. No. 5,728,117, issued to Lash describes a capsulorrhexis instrument that is selectively positionable between a first, retracted position within a tube and a second, extended position projecting out of the tube. The instrument comprises a flexible band having a razor sharp cutting edge which is fixed to a plunger and located within an inserter tube. While in its first, retracted position within the inserter tube, the flexible band assumes an elliptical or oblong shape. However, when the flexible band is moved to its second, extended position outside of the inserter tube such as inside the eye, it deforms into a circular shape whose cutting edge is sufficiently sharp to cut corneal tissue in response to pressure being applied to the corneal tissue by the cutting edge. (While the patent describes corneal tissue being cut, the material to be cut would actually comprise the anterior lens capsule). The dimension to which the flexible band expands to reach the circular shape upon becoming extended from the inserter tube is larger than a cross-section of the gap defined by the inserter tube through which the flexible band travels in its elliptical or oblong shape.

However, none of these apparatus adequately perform their job and are sufficiently complicated and expensive. As a result, there exists a need for a surgical instrument to safely, reliably and consistently create a precise circular anterior capsulorrhexis of proper diameter.

OBJECTS OF THE INVENTION

It is therefore an object of the invention to provide an improved incising apparatus for use in cataract surgery.

Another object of the invention is to provide an improved incising apparatus for use in cataract surgery that can pass through the outer layer of the eye of a patient through a reduced size incision.

A still further object of the invention is to provide an improved incising apparatus for use in cataract surgery that collapses so as to be inserted through a reduced size incision in the patient's eye, but expands when desired to provide a preferred size incising apparatus.

Still other objects and advantages of the invention will in part be obvious and will in part be apparent from the specification and the drawings.

SUMMARY OF THE INVENTION

Generally speaking, in accordance with the invention, an incising apparatus for use in the field of ophthalmology, and more specifically for use during cataract surgery is provided. An incising apparatus for making a circular incision in the anterior lens capsule to obtain access to the native lens for extraction is disclosed. The instrument comprises a safe, simple, inexpensive device, and includes a handle and a circular band with a sharp bottom edge that is deformable upon compression into a very thin, almost flattened ellipse. The invention differs from existing prior art instruments in that it involves no intricate hinges or moving parts, and that it may be inserted through a narrower incision in the outer layers of the eye of a patient. Thus, the incising apparatus of the invention is much less complex, more durable, safer, easier to manufacture and more cost-effective than prior art apparatuses. It is intended for single usage in its preferred embodiment, and is therefore disposable.

BRIEF DESCRIPTION OF THE DRAWINGS

For a more complete understanding of the invention, reference is made to the following description and accompanying drawings, in which:

FIG. 3A is a plan view of an incising apparatus constructed in accordance with a second embodiment of the invention;

FIG. 3B depicts a circular cutting band of the incising apparatus of FIG. 3A;

FIG. 3C depicts the circular cutting band of FIG. 3B positioned on a handle of the incising apparatus of FIG. 3A;

DETAILED DESCRIPTION OF THE PREFERRED EMBODIMENT

Figures 1A, 1B, 1C:
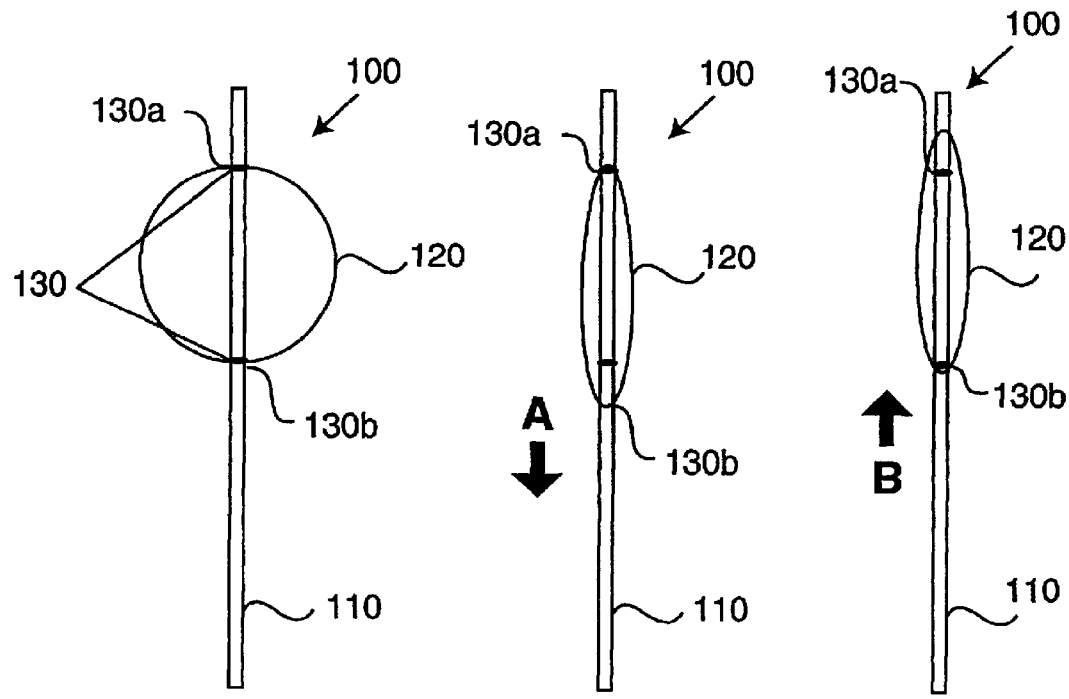
FIG. 1A is a plan view of an incising apparatus constructed in accordance with the invention.
FIGS. 1B and 1C depict the incising apparatus of FIG. 1A in various compressed states.
Figures 2A, 2B:
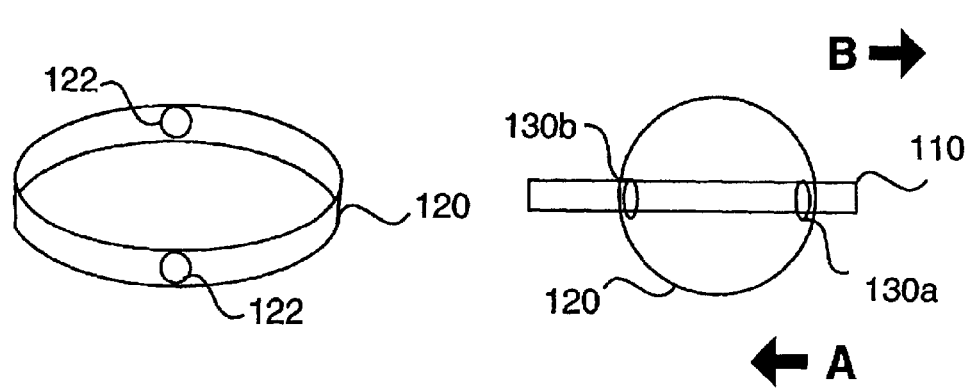
FIG. 2A depicts a circular cutting band of the incising apparatus of FIG. 1A.
FIG. 2B depicts the circular cutting band of FIG. 2A positioned on a handle of the incising apparatus of FIG. 1A.

Referring first to FIGS. 1–2A, an incising apparatus 100 constructed in accordance with a first embodiment of the invention is shown. As is first depicted in FIG. 1, incising apparatus 100 comprises a handle portion 110, a circular cutting band 120, and a pair of stoppers 130 (130a, 130b) positioned along handle 110, along the interior circumference of circular cutting band 120, and positioned so that circular cutting band 120 is maintained in its circular shape. Circular cutting band 120 is slidably attached to handle 110 so that, as noted above, stoppers 130 are positioned inside the circular cutting band. Therefore, as shown in FIG. 1A, the top portion of the circular cutting band in the vicinity of stopper 130a can move in a direction up in FIG. 1A, but is restricted from moving down along handle 110 by stopper 130a. Similarly, the bottom portion of circular cutting band 120 in the vicinity of stopper 130B is able to slide along handle 110 in a downward position in FIG. 1A, but is restricted in its motion moving up in FIG. 1A along handle 110 by stopper 130b. In a preferred embodiment, circular band 120 has one circular edge thereof as a cutting edge therefore being sharpened, and the other circular edge thereof not being designed for cutting, and therefore being blunted. However, it is possible to provide a cutting edge on both sides of circular band 120 as desired and if necessary.

During use, incising apparatus 100 is inserted or removed from a patient's eye through a standard 2.0–3.0 mm corneal or corneal-scleral incision. Alternatively, incising apparatus 100 may be inserted through the corneal side (paracentesis) port of approximately 1.5 mm. The instrument is preferably inserted in a direction so that the circular band is positioned perpendicular, through a 90° rotation with respect to the direction of the incision, so as to prevent any sharp cutting edge of the band from contacting the edges of the incision, and thereby making an additional incision in the patient's eye.

Upon inserting the instrument, a force is encountered when putting the circular band of 5–6 mm in a preferred embodiment through the smaller incision, a compressing force is exerted on the band in a downward direction, such as that of arrow A in FIG. 1B. This force is exerted on band 120, urging it therefore in the direction of arrow A. However, because of the positioning of stopper 130a, the top portion of band 120 in the vicinity of stopper 130a is unable to slide along handle 110 in the direction of arrow A. However, the portion of circular band 120 in the vicinity of stopper 130b is able to slide along handle 110, away from the position of stopper 130b. Therefore, as is shown in FIG. 1B, in accordance with creases preferably provided and positioned at the 12 and 6 o'clock positions of band 120 and extending perpendicular to the coaxial direction of band 120 (at a position in the vicinity of stoppers 130a and 130b), and coextensive with holes 122 of circular band 120 shown in FIG. 2A, band 120 is elongated through the movement of the portion thereof in the vicinity of stopper 130a in the direction of arrow A in FIG. 1B. However, the creases need not be provided. An elongated elliptical shape is therefore formed based upon the force exerted on band 120 upon insertion through the noted incision. In this way, the overall diameter of the band is reduced so that the insertion of a band that will cut an incision of a 5–6 mm circular diameter may be made through a standard 2.0–3.0 mm incision, or smaller without difficulty.

Once inserted into the anterior chamber of the eye, and the force of insertion is no longer present on circular cutting band 120, band 120 slowly springs back to its natural circular shape, the portion of band 120 in the vicinity of stopper 130b sliding along handle 110 back towards stopper 130b in the direction opposite that of arrow A in FIG. 1B. Therefore, this circular band may take a circular diameter of 5–6 mm, or any other appropriate size. During use, after expanding back to the circular shape, the instrument is forced so that its sharp bottom edge is pressed against the anterior lens capsule, creating a circular incision in a manner such as in the use of a cookie-cutter.

Upon removal of the incising apparatus, a reverse force is exerted on circular cutting band 120, and a compression of the band into an elliptical shape is performed in a direction opposite to that during insertion. Specifically, upon removal of the incising apparatus through the incision in the patient's eye, handle 110 is pulled in a direction opposite that of arrow B in FIG. 1C. By pulling the circular extended band 120 through the incision in the patient's eye, a force is generated in the direction of arrow B. Because of the position of stopper 130b, the bottom portion of circular band 120 in FIG. 1C cannot move in a direction of arrow B. However, the top portion of circular band 120 can move in a direction sliding along handle 110 in the direction of arrow B, away from stopper 130a. Because of the creases in circular cutting band 120 at the 12 and 6 o'clock positions noted above, the force in the direction of arrow B compresses and elongates circular cutting band 120, so that the band may be removed through the incision. While the use of two stoppers 130 is described, one stopper can also be employed. This single stopper could cover the entire portion of the handle between the depicted positions of stoppers 130a and 130b, therefore functioning identically to the two stopper embodiment.

FIGS. 2A and 2B depict close up views of circular band 120, and stoppers 130a and 130b, as positioned against handle 110. As is shown in FIG. 2A, respective holes 122 are formed in band 120 to allow handle 110 to fit therethrough. FIG. 2B depicts the same band positioned on handle 110, with stoppers 130a and 130b in position. In FIG. 2B, it is more clearly understood that upon generation of a force in the direction of arrow A upon the insertion of the instrument in a patient's eye through an incision, the circular band will elongate away from stopper 130b, while the generation of a force in the direction of arrow B upon the removal of circular band 120 from a patient's eye through an incision will generate an elongated circular band 120 with the elongation taking place in the vicinity of the portion of the band in the vicinity of stopper 130a.

Referring next to FIGS. 3A–3C, an incising apparatus constructed in accordance with a second embodiment of the invention will now be described.

As is shown in FIG. 3A an incising apparatus 200 constructed in accordance with the second embodiment includes a handle 210, a circular band 220, and integral cylindrical stopping faces 230a and 230b. While integral cylindrical stopper faces 230a and 230b function similarly to stoppers 130a and 130b of FIG. 1A, these stopper faces are formed integral with handle 210. Therefore, as is shown in FIG. 3C, integral cylindrical stopper faces 230a and 230b form a transition from a flat compressed portion of handle (compressed portion 210a and 210b of handle 210) and a cylindrical portion 210c of handle 210. Because as is shown in FIG. 3B, circular band 220 is formed with oval holes 222, these oval holes are structured so as to slide freely along flattened portions 210a and 210b of handle 210, but to be restricted in their movement upon contact with integral stopper faces 230b and 230a, setting off cylindrical portion 210c. Therefore, rather than requiring separate stoppers as shown in the first embodiment, circular band 220 will freely slide along the indented portions of handle 210, but will stop in a manner similar to that noted above with respect to the non-integral stoppers upon the reaching of the integral stopper faces defining the cylindrical portion of handle 210.

The incising apparatus of the second embodiment functions in a manner similar to that of the first embodiment. When force is generated in either direction parallel to handle 210, one side of circular band 220 is restricted in its movement against either integral stopper faces 230a or 230b, and the other side of circular band 220 slidably moves relative to indented handle portion 210a or 210b, as the applied force dictates. In this manner, a properly operating device similar to that of FIG. 1 can be provided, but in an easier design not requiring independent stoppers to be affixed to the handle.

Figure 4:
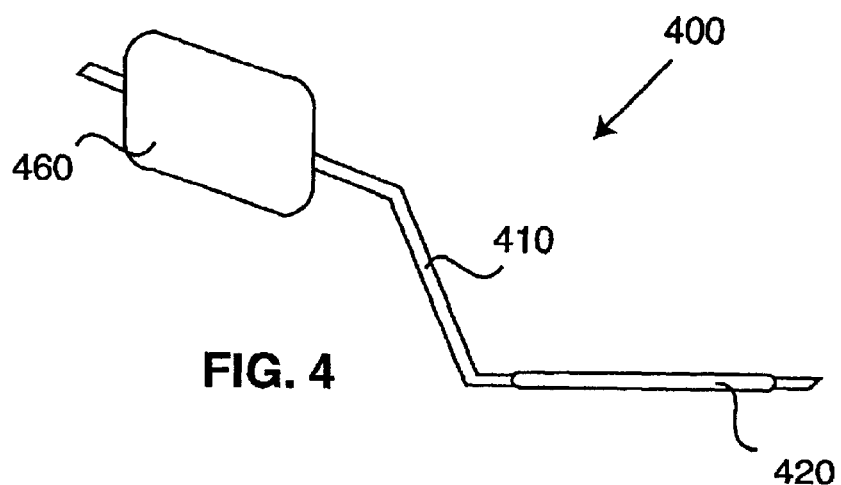
FIG. 4 depicts an incising apparatus handle constructed in accordance with an alternative embodiment of the invention.

Referring next to FIG. 4, an alternative embodiment of the incising apparatus is shown. An incising apparatus 400 includes a circular cutting band 420 and a top handle portion 410 similar to that of the prior embodiment, utilizing either stoppers similar to stoppers 130a and 130b of the first embodiment, or integral stopper faces 230a and 230b of the second embodiment (now shown). Thus, the embodiment shown in FIG. 4 is a modification of the handle included with the first two embodiments, and may be used with any head or circular band portion disclosed in this application.

As is shown in FIG. 4, handle portion 400 is shown in a bent, angled format including an angle to most easily facilitate the surgeon's actions. The angle of the bends in the handle are determined by the patient's anatomy, and several different standard embodiments may be manufactured.

Additionally, custom angle embodiments may also be provided, or adjustable handle positions may be provided as necessary. Furthermore, a flat portion 460 is provided in the vicinity of the end of handle portion 410 opposite that including circular band 420 to allow a surgeon to have a better grip on the handle. The handle of the prior embodiments may include this flat portion, to allow for proper movement and rotation and handling of the apparatus by a surgeon.

Figure 5A:
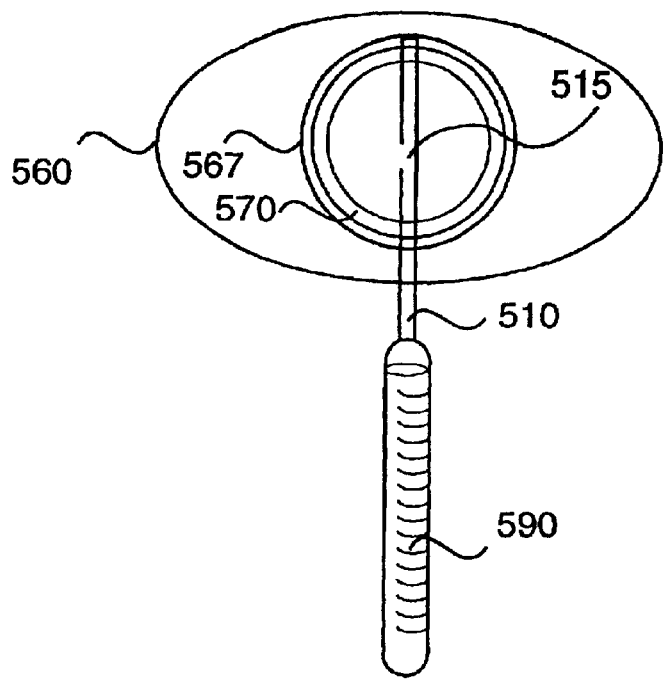
FIGS. 5A and 5B depict an incising apparatus in accordance with a third embodiment of the invention.
Figure 5B:
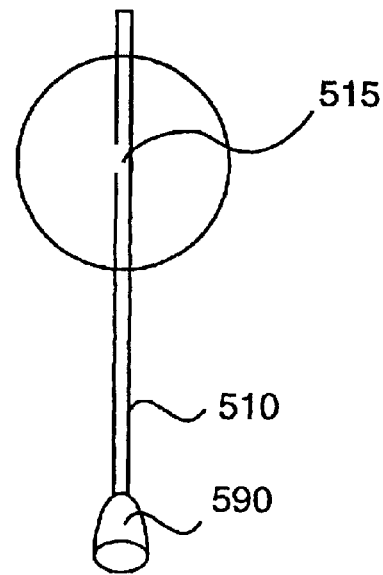

Referring next to FIGS. 5A and 5B, a further embodiment of the invention is shown. This embodiment may be employed using a handle of any of the prior embodiments.

In the type of cataract surgery described above, it is standard practice to inject a viscoelastic material into the eye (560) in the vicinity of iris 565 and anterior lens capsule 570 to aid in performing the anterior capsulorrhexis step, and in order to maintain the proper anterior chamber depth. Often, some of this viscoelastic material is lost during the insertion of instruments into the eye. Further, in performing cataract surgery on dense, opacified lenses, visualization of the anterior capsule is often difficult for the surgeon. Therefore, current techniques advocate the use of an injectable non-toxic dye such as flourescein or indocyanine green to better delineate the margins of the anterior capsular incision.

Therefore, in accordance with the embodiments depicted in FIGS. 5A and 5B, the entire shaft of the instrument is provided hollowed out. The proximal end of a handle 510 is designed for attachment to a syringe 590 which may contain viscoelastic material, dye or other fluid so that if necessary, this viscoelastic material or dye may be injected into the eye 560 even after the instrument has been placed inside the eye. Therefore, as is shown in FIG. 5A, as well as FIG. 5B, handle 510 includes a hollow coaxial center, and a hole 515 is provided at the end of handle 510 opposite the end adapted for connection to syringe 590. Through this hole, various material included within syringe 590 may be injected into a patient's eye as necessary. This material can be injected into the eye without having to remove the instruments from the eye as required in the prior art, and therefore is able to accurately maintain the optimal anterior chamber depth and aid in capsular visualization, respectively. While only one hole 515 is shown in FIGS. 5A and 5B, any number of holes 515 as desired could be provided.

Figure 6:
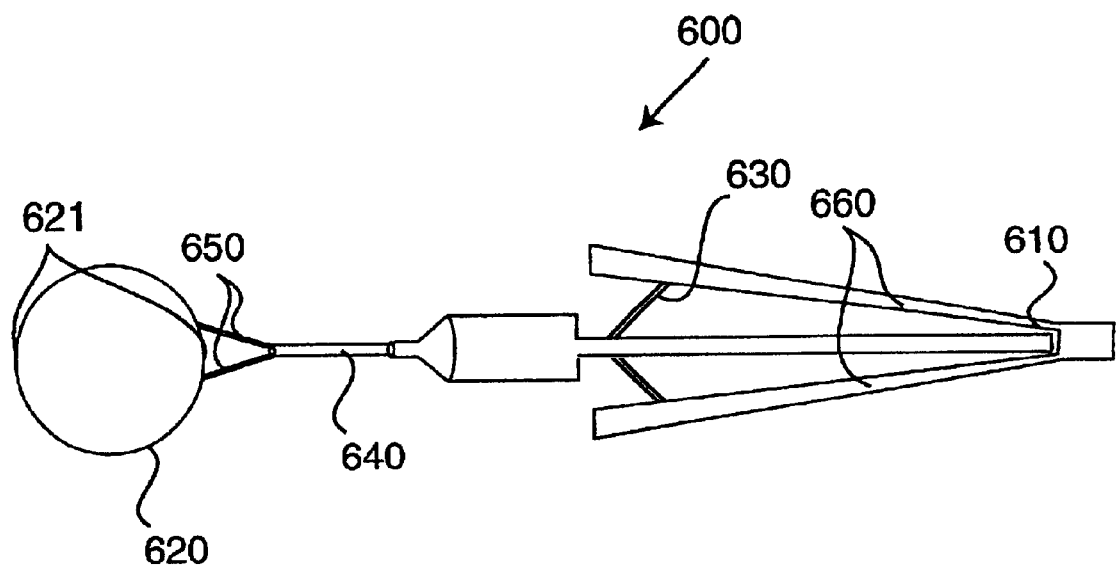
FIGS. 6 and 7 depict an incising apparatus in accordance with a fourth embodiment of the invention.
Figure 7:
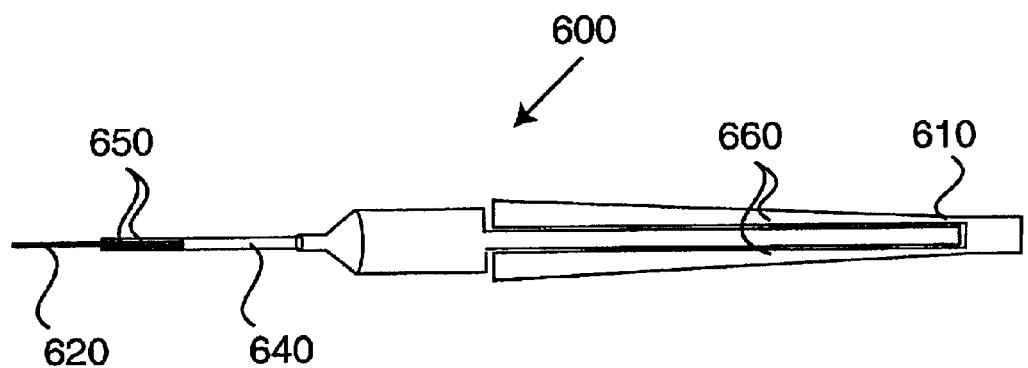

Referring next to FIGS. 6 and 7, an incising apparatus constructed in accordance with a third embodiment of the invention is shown.

As is shown in FIG. 6, an incising apparatus 600 includes a gripping handle 610 having pressure members 660, and biasing members 630. FIG. 6 shows handle 610 in an open position. Also included is a tubular component 640, and two arms 650 protruding from a distal end thereof. A circular cutting ring 620 is attached to the two arms, which as shown in 600 are open in their natural state, but which may be compressed together like forceps by the compression of pressure members 660. Circular cutting band 620 is provided with creases 621 at the 6 and 12 o'clock positions as shown in the prior embodiments. Upon compression of pressure members 660 against the force of biasing members 630, the structure of incising apparatus 600 changes to that shown in FIG. 7. As is shown in FIG. 7, elements 660 have been compressed against the biasing force of bias springs 630 through an internal mechanism included within tubular component 640 and have compressed arms 650 towards each other, thus also flattening cutting ring 620. The arms are specifically attached to the dorsal side of the cutting ring so as to prevent the unintended contact with various eye structures and to enable the instrument's proper action. In the closed state in FIG. 7, the cutting ring may be inserted into a small incision in a patient's eye, and then upon the release of pressure on handle 610, ring 620 will be returned to its original circular position and available for cutting as above in the prior embodiments.

In accordance with this embodiment, the outer tubular member is directed distally upon compression of the instrument handle. This forward outer movement of the outer tube 640 encases the two arms within tubular component 640, thereby squeezing them together and flattening the ring. In this embodiment, the instrument's handle is grasped and compressed by the surgeon prior to and during insertion of the instrument into the eye. Once the ring is fully inserted into the eye, the surgeon releases the force of compression of the instrument, thereby allowing the ring to spring open and be depressed against the anterior lens capsule as previously described. After achieving the desired result, the surgeon then compresses the handle once again, flattening the ring and removing the instrument. The tubular dimensions may be extremely small, such as 21 gauge (0.80 mm), thereby enabling insertion of the instrument through even the narrow paracentesis side port. The tube may also be curved to achieve an optimal angle for instrument action. The instrument in this embodiment may be manufactured of a disposable or reusable sterilized material. Further, the cutting rings may be manufactured to be disposable and replaceable and to be inserted onto the two V arms via a clip on or any other standard mechanism. In this embodiment, the handle and other components of apparatus 600 would be reusable, other than cutting ring 620.

All the embodiments of the invention provide various advantages over the prior art. As the field of cataract surgery progresses, it becomes more feasible to perform various procedures through smaller corneal or corneal-scleral incisions. A smaller incision is desirable, as it decreases the risks involved in the procedure. In prior related devices, the corneal incision is limited in size, because it must be at least large enough to engage the tubing and cutter, cutting end or cross hatch of the prior art devices noted above. The size of these devices therefore force the surgeon to create a corneal incision that may be larger than otherwise necessary or beneficial for the procedure.

The device in accordance with the invention is not limited in how small it may be. It is simple in structure and is able to be manufactured in any size, fitting even the narrowest of incisions such as a paracentesis port. Also, other prior art devices neglect to provide a means for selectively reinflating the anterior chamber with viscoelastic or for injecting dye while the instrument is inside the eye passing through a reduced size incision in the eye, leading to inferior conditions for successful anterior capsulorrhexis, in part because the instruments may need to be removed during the procedure prior to completion. In addition, prior related instruments are complex, involving several moving interconnected parts. This may lead to an increased risk of surgeon error or mechanical failure. Further, this complexity adds to manufacturing cost, and has restricted the large scale production and usage of these other expensive instruments.

It will thus be seen that the objects set forth above, among those made apparent from the preceding description, are efficiently attained and, because certain changes may be made in the above constructions without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention hereindescribed and all statements of the invention which, as a matter of language, might be said to fall therebetween.

What is claimed is:

1. An incising apparatus, comprising:
    a handle having a proximal end and a distal end;
    one or more pressure members formed at said proximal end of said handle;
    two arms extending from said distal end of said handle; and
    a circular cutting band attached to said two arms, said circular cutting band being provided with two creases, one of said creases being provided between the portions of said cutting band attached to said two arms, the other of said creases being provided on said cutting band at a position of said cutting band across the diameter thereof from said first crease; wherein upon compression of said pressure members, said two arms are compressed together, thereby flattening said circular cutting band along said two creases.

2. The incising apparatus of claim 1, wherein said pressure members are biased in an opened position.

3. The incising apparatus of claim 2, wherein said circular cutting member is maintained in a circular shape when said pressure members are in their biased opened state.

4. The incising apparatus of claim 1, further comprising a tubular member provided adjacent a meeting location of said two arms, wherein upon compression of said pressure members said tubular member slides towards said distal end of said handle, thus compressing said two arms together.

5. The incising apparatus of claim 4, further comprising biasing members biasing said pressure members open.

6. The incising apparatus of claim 5, wherein upon compression of said pressure members, said biasing members slide said tubular member toward said distal end of said handle.

* * * * *